United States Patent
Mitsuhashi

(10) Patent No.: US 9,993,143 B2
(45) Date of Patent: Jun. 12, 2018

(54) CAPSULE ENDOSCOPE AND CAPSULE ENDOSCOPE SYSTEM

(71) Applicant: OLYMPUS CORPORATION, Tokyo (JP)

(72) Inventor: Kei Mitsuhashi, Nishitokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days. days.

(21) Appl. No.: 15/291,190

(22) Filed: Oct. 12, 2016

(65) Prior Publication Data

US 2017/0027425 A1 Feb. 2, 2017

Related U.S. Application Data

(63) Continuation of application No. PCT/JP2015/077074, filed on Sep. 25, 2015.

(30) Foreign Application Priority Data

Nov. 27, 2014 (JP) .................................. 2014-240323

(51) Int. Cl.
*A61B 1/06* (2006.01)
*A61B 1/00* (2006.01)
(Continued)

(52) U.S. Cl.
CPC ............ *A61B 1/041* (2013.01); *A61B 1/0002* (2013.01); *A61B 1/00016* (2013.01);
(Continued)

(58) Field of Classification Search
CPC ... A61B 1/041; A61B 1/00016; A61B 1/0002; A61B 1/00036; A61B 1/045;
(Continued)

(56) References Cited

U.S. PATENT DOCUMENTS 8,164,659 B2 * 4/2012 Mori .................. A61B 1/00009
348/245
2005/0025368 A1 2/2005 Glukhovsky
(Continued)

FOREIGN PATENT DOCUMENTS

CN 101179725 A 5/2008
CN 101365986 A 2/2009
(Continued)

OTHER PUBLICATIONS

International Search Report dated Dec. 22, 2015 issued in PCT/JP2015/077074.

*Primary Examiner* — Anhtuan T Nguyen
*Assistant Examiner* — William Chou
(74) *Attorney, Agent, or Firm* — Scully, Scott, Murphy & Presser, P.C.

(57) ABSTRACT

A capsule endoscope includes an image pickup device, a memory configured to store brightness information acquired by the image pickup device, and a control section configured to perform control to compare the brightness information acquired by the image pickup device with brightness information acquired by the image pickup device immediately before acquiring the brightness information and stored in the memory, cause the image pickup device to acquire brightness information when the comparison result is no greater than a threshold, compare the acquired brightness information with the brightness information acquired by the image pickup device immediately before and stored in the memory, and cause the image pickup device to pick up an image when the comparison result is greater than the threshold and cause the memory to store the picked-up image or cause an image transmitting section provided in the capsule endoscope to transmit the image to outside the capsule endoscope.

9 Claims, 7 Drawing Sheets

(51) Int. Cl.
A61B 1/04 (2006.01)
H04N 5/225 (2006.01)
H04N 5/232 (2006.01)
H04N 5/243 (2006.01)
A61B 1/045 (2006.01)
H04N 5/235 (2006.01)

(52) U.S. Cl.
CPC .......... *A61B 1/00036* (2013.01); *A61B 1/045* (2013.01); *A61B 1/0661* (2013.01); *H04N 5/225* (2013.01); *H04N 5/232* (2013.01); *H04N 5/2351* (2013.01); *H04N 5/23206* (2013.01); *H04N 5/23241* (2013.01); *H04N 5/243* (2013.01); *A61B 1/00006* (2013.01); *H04N 2005/2255* (2013.01)

(58) Field of Classification Search
CPC ...... A61B 1/0661; H04N 5/225; H04N 5/232; H04N 5/23241; H04N 5/243
USPC ................ 600/109, 117, 118, 160, 178, 180; 382/128; 348/45
See application file for complete search history.

(56) References Cited

U.S. PATENT DOCUMENTS

| | | | |
|---|---|---|---|
| 2008/0287742 | A1 | 11/2008 | St. George et al. |
| 2012/0271104 | A1 | 10/2012 | Khait et al. |
| 2013/0314518 | A1* | 11/2013 | Mitsuhashi ........ A61B 1/00009 348/68 |
| 2015/0073213 | A1 | 3/2015 | Khait et al. |

FOREIGN PATENT DOCUMENTS

| | | |
|---|---|---|
| EP | 1492352 A2 | 12/2004 |
| JP | 2005-020755 A | 1/2005 |
| JP | 2008-264539 A | 11/2008 |
| JP | 2013-511320 A | 4/2013 |
| WO | 2011/061746 A1 | 5/2011 |

* cited by examiner

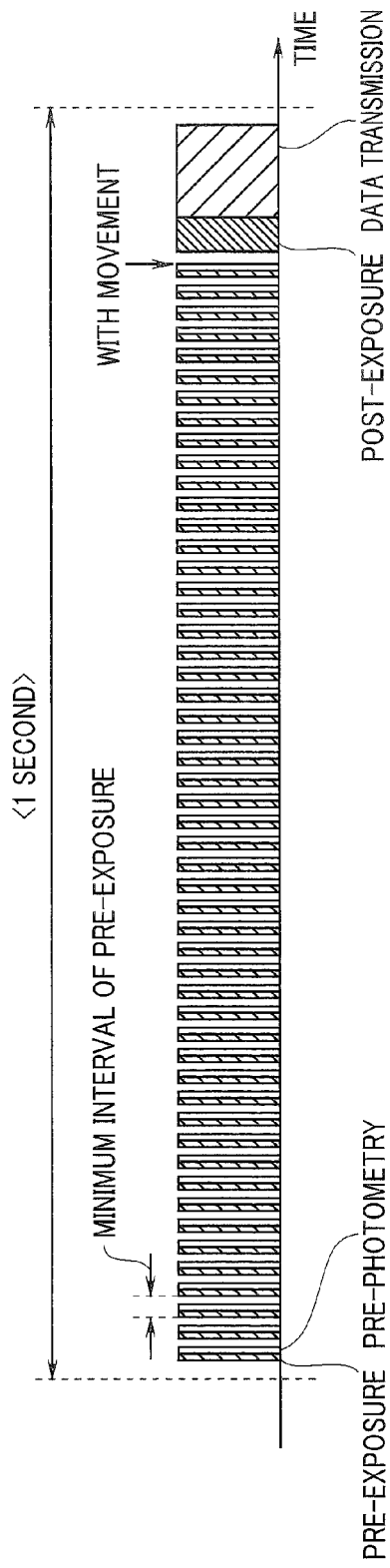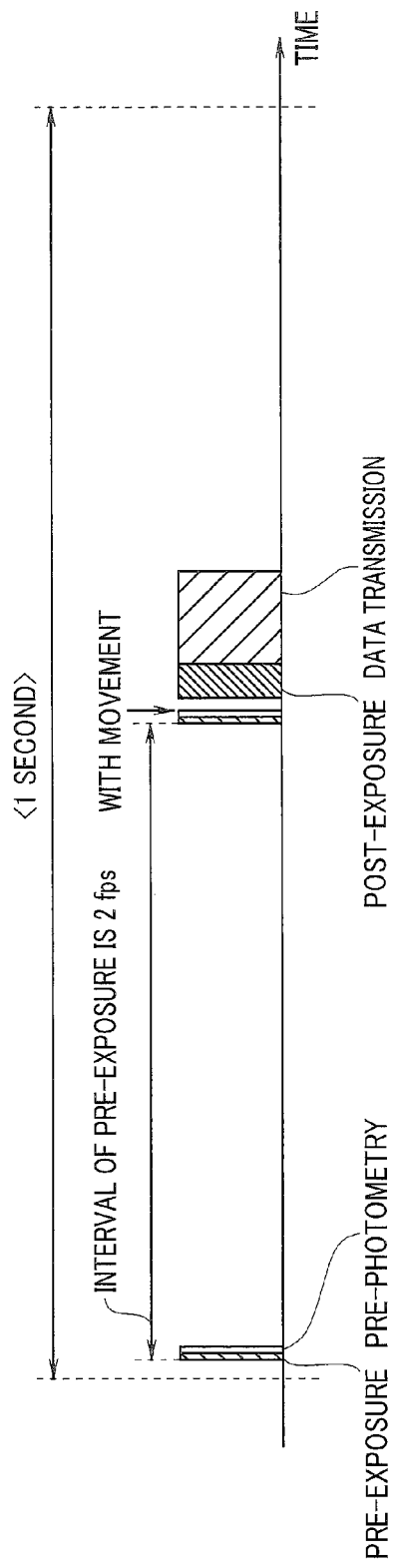

CAPSULE ENDOSCOPE AND CAPSULE ENDOSCOPE SYSTEM

CROSS REFERENCE TO RELATED APPLICATION

This application is a continuation application of PCT/JP2015/077074 filed on Sep. 25, 2015 and claims benefit of Japanese Application No. 2014-240323 filed in Japan on Nov. 27, 2014, the entire contents of which are incorporated herein by this reference.

BACKGROUND OF THE INVENTION

1. Field of the Invention

The present invention relates to a capsule endoscope and a capsule endoscope system configured to be introduced into a subject and be able to acquire in-vivo information.

2. Description of the Related Art

Endoscopes in a medical field are conventionally used for in-vivo observation or the like. As one such endoscope, a capsule endoscope has been proposed in recent years which is disposed in a body cavity when swallowed by a subject, picks up images of the subject while moving through the body cavity along with a peristaltic movement, and can wirelessly send picked-up images of the subject to outside as image pickup signals.

Such a capsule endoscope, in general, often photographs two frames per second. Photographing of two frames per second is set because the capsule endoscope is retained in the body cavity for a considerably long period of time, while the capacity of a battery incorporated in the capsule endoscope is limited.

Movement of the capsule endoscope in the body cavity depends on peristaltic movement or the like, and so it is highly probable that the capsule endoscope may be retained in a specific place in the body cavity for a long period of time. On the other hand, since images are periodically picked up even during the retention period, completely identical images may be repeatedly acquired. However, only one frame of these images is sufficient to contribute to diagnosis and other images are wasted.

Therefore, Japanese Patent Application Laid-Open Publication No. 2005-20755 proposes a capsule endoscope configured to compare photographed images with last transmitted images, transmit only photographed images which are substantially different from the last photographed images to an external receiving apparatus to thereby save energy consumed.

SUMMARY OF THE INVENTION

A capsule endoscope according to an aspect of the present invention includes an image pickup section, a storage section configured to store brightness information acquired by the image pickup section, and a control section configured to perform control so as to compare the brightness information acquired by the image pickup section with brightness information acquired by the image pickup section immediately before acquiring the brightness information and stored in the storage section, cause the image pickup section to acquire brightness information when the comparison result is equal to or less than a threshold, compare the acquired brightness information with the brightness information acquired by the image pickup section immediately before and stored in the storage section, and cause the image pickup section to pick up an image when the comparison result is greater than the threshold, and cause the storage section to store the image or cause a transmitting section provided in the capsule endoscope to transmit the image to outside the capsule endoscope.

A capsule endoscope system according to an aspect of the present invention includes a capsule endoscope including an image pickup section, a storage section configured to store brightness information acquired by the image pickup section, and a control section configured to perform control so as to compare the brightness information acquired by the image pickup section with brightness information acquired by the image pickup section immediately before acquiring the brightness information and stored in the storage section, cause the image pickup section to acquire brightness information when the comparison result is equal to or less than a threshold, compare the acquired brightness information with the brightness information acquired by the image pickup section immediately before and stored in the storage section, and when the comparison result is greater than the threshold, cause the image pickup section to pick up an image and cause the storage section to store the image or cause a transmitting section provided in the capsule endoscope to transmit the image to outside the capsule endoscope, and an external apparatus including a receiving section configured to receive the image transmitted to outside by the transmitting section and an external storage section configured to store the image received by the receiving section.

BRIEF DESCRIPTION OF THE DRAWINGS

FIG. 5A is a diagram for describing an interval of pre-exposure;

FIG. 5B is a diagram for describing an interval of pre-exposure;

FIG. 7 is an enlarged view of a pre-exposure area 13a; and

DETAILED DESCRIPTION OF THE PREFERRED EMBODIMENT(S)

Hereinafter, embodiments of the present invention will be described with reference to the accompanying drawings.

First Embodiment

Figure 1:
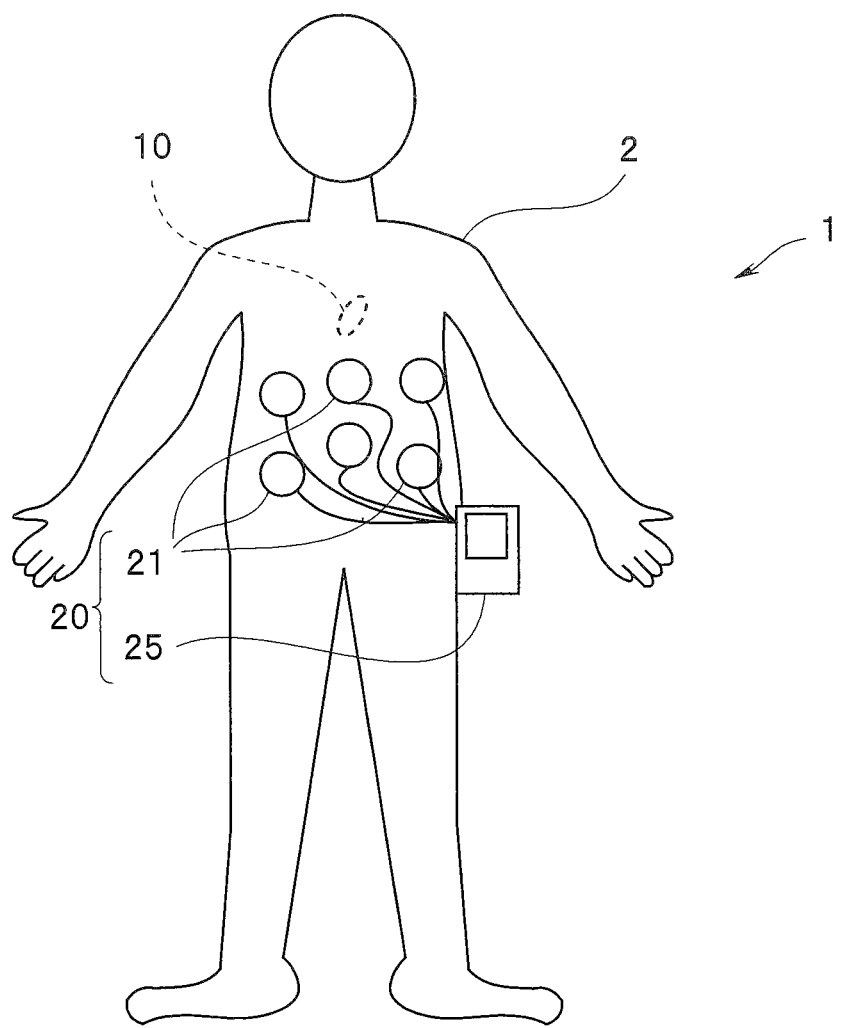
FIG. 1 is a diagram for describing a usage form of an endoscope system according to a first embodiment.
Figure 2:
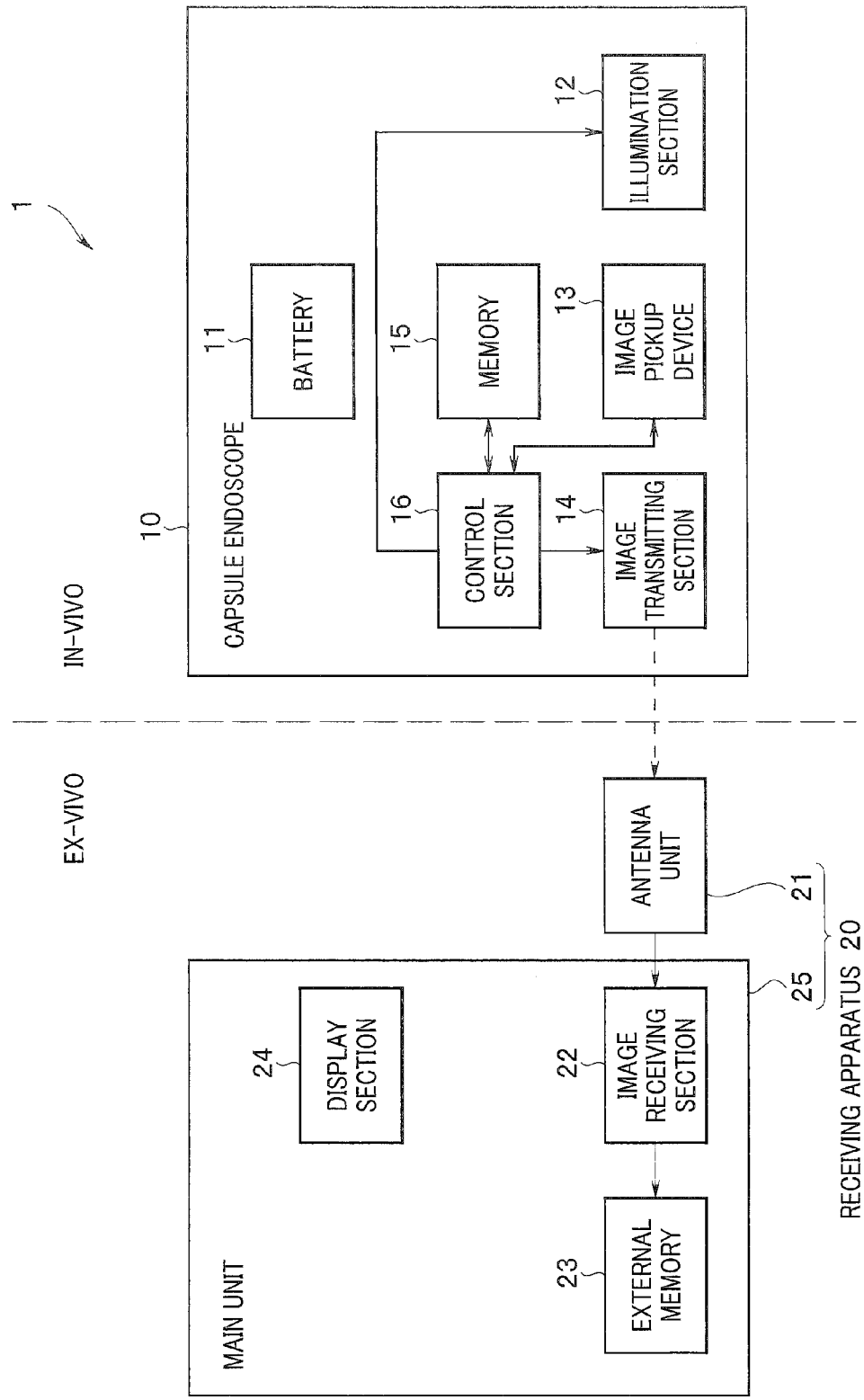
FIG. 2 is a diagram for describing a detailed configuration of a capsule endoscope and a receiving apparatus according to the first embodiment.
Figure 3:
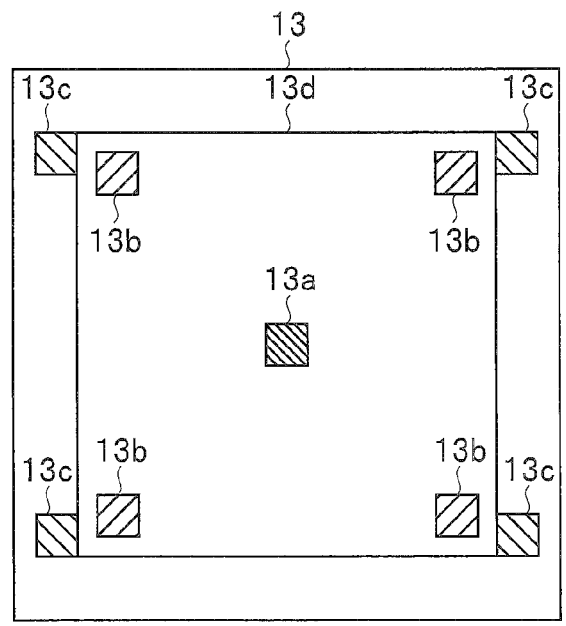
FIG. 3 is a diagram for describing a pre-exposure area for performing pre-exposure.
Figure 4:
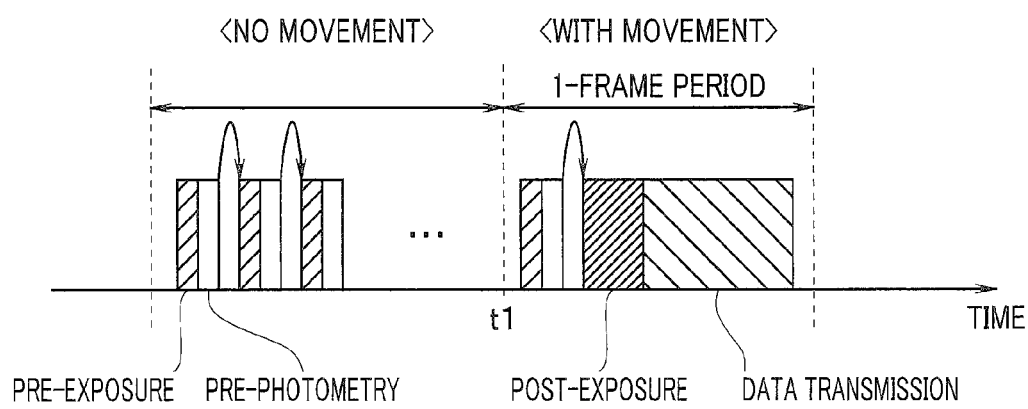
FIG. 4 is a diagram for describing exposure timing.

First, a configuration of an endoscope system according to a first embodiment of the present invention will be described using FIG. 1 to FIG. 5B. FIG. 1 is a diagram for describing a usage form of the endoscope system according to the first embodiment, FIG. 2 is a diagram for describing a detailed configuration of the capsule endoscope and a receiving apparatus according to the first embodiment, FIG. 3 is a diagram for describing a pre-exposure area for performing pre-exposure, FIG. 4 is a diagram for describing exposure timing and FIGS. 5A and 5B are diagrams for describing an interval of pre-exposure.

As shown in FIG. 1, an endoscope system 1 which is a capsule endoscope system is constructed of a capsule endoscope 10 and a receiving apparatus 20 as an external apparatus.

The capsule endoscope 10 is introduced into an in-vivo digestive organ lumen by being swallowed by an examinee 2. The capsule endoscope 10 includes, as shown in FIG. 2, a battery 11, an illumination section 12 configured to illuminate an object, an image pickup device 13 as an image pickup section configured to pick up an image of the object, an image transmitting section 14 configured to wirelessly transmit the image pickup signal (endoscope image), a memory 15 as a storage section configured to temporarily store a photometric result, which will be described later, and a control section 16 configured to control the entire capsule endoscope 10, all of which are accommodated in a case, to constitute main parts.

On the other hand, the receiving apparatus 20 disposed outside the body of the examinee 2 includes an antenna unit 21 configured to receive an image pickup signal from the capsule endoscope 10 and a main unit 25, for example, to be worn on the waist of the examinee 2. The main unit 25 is constructed, as shown in FIG. 2, of an image receiving section 22 configured to receive an image pickup signal (endoscope image) wirelessly transmitted from the capsule endoscope 10 via the antenna unit 21, an external memory 23 as an external storage section configured to store the endoscope image received by the image receiving section 22 via the antenna unit 21, and a display section 24 configured to display the endoscope image received by the image receiving section 22 or the endoscope image stored in the external memory 23.

The capsule endoscope 10 of the present embodiment performs pre-exposure and then photometry before performing image pickup. That is, the control section 16 causes the illumination section 12 provided in the capsule endoscope 10 to emit light and causes the image pickup device 13 to pick up an image. The control section 16 acquires brightness information of the image (that is, performs photometry) from only part of pixel information of a pre-exposure area, which will be described later, without using all pixel information of the image pickup device 13 in this image pickup. Note that photometry performed using pixel information of the pre-exposure area is also called pre-photometry in the following description.

As shown in FIG. 3, a pre-exposure area 13a is provided so as to include a central pixel of the image pickup device 13 and the control section 16 acquires brightness information based on the pixel information of this part, that is, information obtained from the pre-exposure area 13a. Note that the pre-exposure area provided in the image pickup device 13 is not limited to the pre-exposure area 13a provided so as to include the central pixel.

For example, four pre-exposure areas 13b may be provided near four corners on a plane on which the image pickup device 13 is disposed and the control section 16 may acquire brightness information based on information obtained from the four pre-exposure areas 13b.

Furthermore, four pre-exposure areas 13c may be provided at positions which are in adjacent areas of the pixel region 13d used to display pixels of the image pickup device 13 and not reproduced or displayed on a monitor screen, and the control section 16 may acquire brightness information based on information obtained from the four pre-exposure areas 13c. That is, the pre-exposure areas 13c are provided in regions called "optical black" which are provided outside the pixel region 13d used for display to detect black.

Furthermore, the control section 16 is not limited to acquisition of brightness information based on information obtained from the pre-exposure areas 13a, 13b or 13c, but the control section 16 may acquire the brightness information by combining the pre-exposure area 13a and the four pre-exposure areas 13b and based on information obtained from the pre-exposure areas 13a and 13b.

The control section 16 temporarily stores the brightness information (pre-photometric result) acquired in this way in the memory 15. As shown in FIG. 4, when the pre-photometric operation ends, the control section 16 performs the next pre-exposure and pre-photometric operation. The pre-exposure and pre-photometric operation have the aforementioned contents and the same pre-exposure and pre-photometric operation are performed.

Here, an interval of pre-exposure will be described using FIG. 5A and FIG. 5B. In the present embodiment, the following two patterns are assumed about the interval of pre-exposure, but other patterns may be adopted without being limited to this.

As shown in FIG. 5A, a first pattern is one in which the interval of pre-exposure is minimized, that is, the interval of pre-exposure is made as short as possible. Minimizing the interval of pre-exposure makes it possible to prevent movement of the capsule endoscope 10 from being overlooked.

That is, conventional capsule endoscopes acquire pickup images of 2 frames per second, but in FIG. 5A, the interval of pre-exposure is minimized and when the capsule endoscope 10 moves, it is possible to acquire pickup images of 3 or more frames per second and prevent lesioned regions or the like from being overlooked.

A second pattern is one shown in FIG. 5B in which the interval of pre-exposure is set to a predetermined interval. Note that in the example in FIG. 5B, the interval of pre-exposure is set to 2 fps, but the interval of pre-exposure is not limited to this and may be set to other intervals. In the case of the example in FIG. 5B, when movement of the capsule endoscope 10 is found, pickup images of 2 frames per second are acquired as in the case of the prior art, but when no movement is found in the capsule endoscope 10, pickup images of 1 frame per second are acquired or no pickup image is acquired at all, and it is thereby possible to reduce power consumption of the capsule endoscope 10 compared to the prior art.

The control section 16 compares brightness information obtained by second pre-photometry with the last brightness information stored in the memory 15. More specifically, the control section 16 calculates a difference value between the brightness information obtained by the second pre-exposure and the last brightness information stored in the memory 15. When the comparison result falls within a predetermined threshold, the control section 16 determines that the capsule endoscope 10 has not moved (is retained) for a period between two photometric operations. Upon determining that the capsule endoscope 10 has not moved, the control section 16 further proceeds to the next pre-exposure and pre-photometric operation. While repeating such pre-exposure and pre-photometric operation, if the comparison result between the latest brightness information and the last brightness information exceeds a predetermined threshold, the control section 16 determines that the capsule endoscope 10 has moved.

Note that when, for example, there are a plurality of pre-exposure areas such as the pre-exposure areas 13b or 13c, the control section 16 determines the movement of the capsule endoscope 10 from a change in the brightness information of each pre-exposure area. When the brightness information in each pre-exposure area changes even at least one location, the control section 16 determines that the capsule endoscope 10 has moved. Note that the control section 16 may also determine that the capsule endoscope 10 has moved when all the brightness information in each pre-exposure area has changed.

For example, as shown in FIG. 4, when a comparison result between the brightness information obtained by a pre-exposure after time t1 and the last brightness information exceeds a predetermined threshold, the control section 16 determines that the capsule endoscope 10 has moved, and performs image pickup, that is, post-exposure following the pre-photometric operation. During the image pickup, all the pixel information of the image pickup device 13, here substantially all the pixel information including all pixels which become images displayed on the monitor is acquired.

The control section 16 applies predetermined signal processing to pixel information acquired by the image pickup device 13 and outputs an image signal acquired to the image transmitting section 14. The image transmitting section 14 wirelessly transmits the image signal to which predetermined signal processing is applied by the control section 16 to the external receiving apparatus 20. Note that although the image transmitting section 14 transmits the image signal to the external receiving apparatus 20, the image signal may be stored in the memory 15 in the capsule endoscope 10 via the control section 16.

The wirelessly transmitted image signal is received by the image receiving section 22 via the external antenna unit 21. The image receiving section 22 stores the received image signal in the external memory 23 or outputs the received image signal to the display section 24 to display an endoscope image. Note that upon receiving the image signal (endoscope image) from the capsule endoscope 10, the receiving apparatus 20 may add a time stamp to the endoscope image and store the endoscope image with the time stamp in the external memory 23.

When a series of processes from image pickup to image transmission end, the control section 16 resumes the pre-exposure and pre-photometric operation and repeats the aforementioned processes. That is, the control section 16 compares the brightness information obtained as a result of pre-photometry with the brightness information stored in the memory 15, that is, latest brightness information, an image of which is determined to be picked up since an immediate preceding image is picked up, and determines whether or not the capsule endoscope 10 has moved. Upon determining that the capsule endoscope 10 has not moved, the control section 16 continues pre-exposure and pre-photometric operation and picks up an image with post-exposure upon determining that the capsule endoscope 10 has moved, and transmits data of the image signal obtained.

Next, operation of the capsule endoscope 10 configured as shown above will be described.

Figure 6:
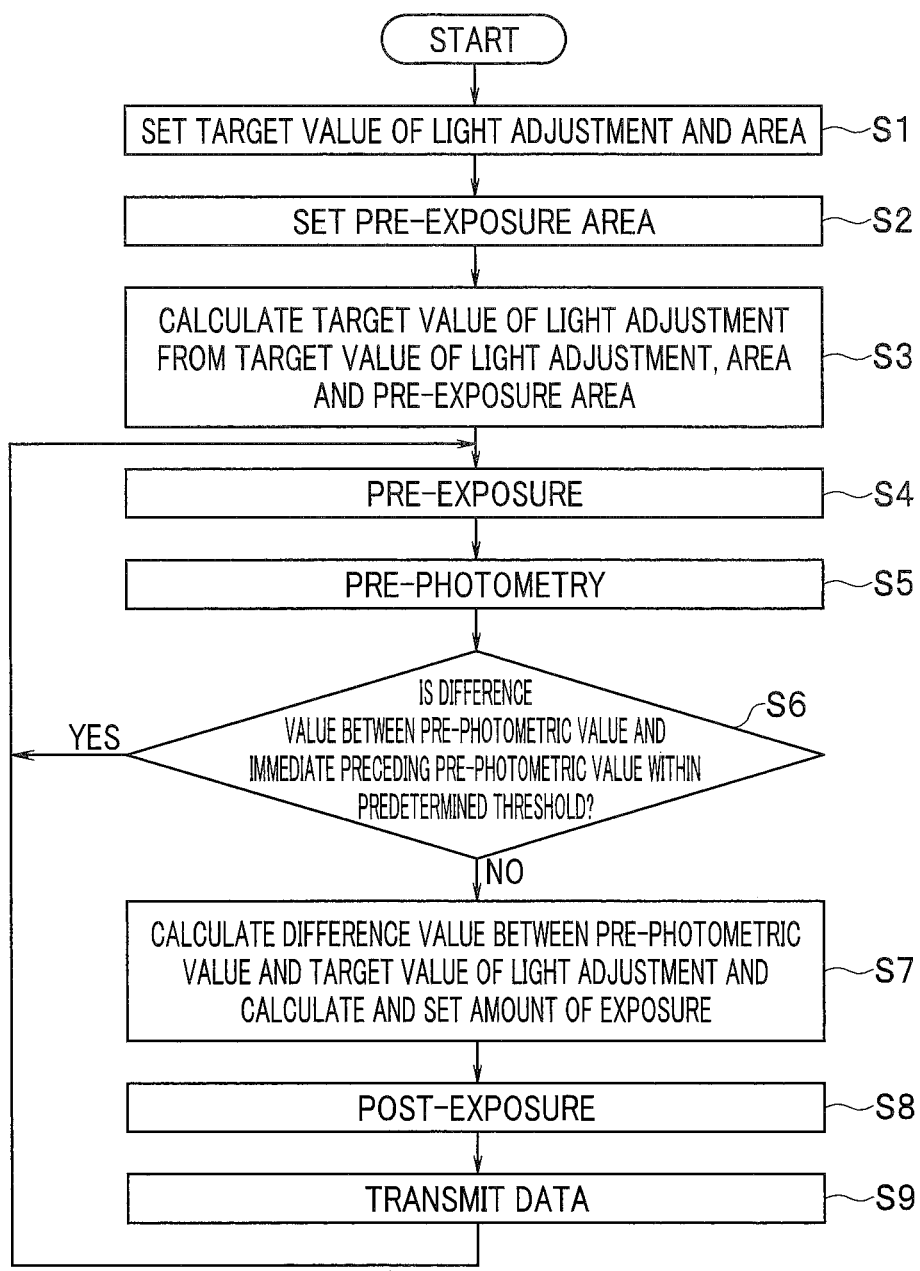
FIG. 6 is a flowchart for describing operation of the capsule endoscope 10 according to the first embodiment.

FIG. 6 is a flowchart for describing operation of the capsule endoscope 10 according to the first embodiment.

First, a target value of light adjustment and an area are set (step S1) and a pre-exposure area is set (step S2). Next, a target value of light adjustment is calculated from the target value of light adjustment and the area and the pre-exposure area (step S3). Next, pre-exposure is executed (step S4) and pre-photometry is executed (step S5).

It is determined whether or not a difference value between the pre-photometric value and an immediate preceding pre-photometric value falls within a predetermined threshold (step S6). When the difference value between the pre-photometric value and the immediate preceding pre-photometric value falls within the predetermined threshold, the result is YES, the flow returns to step S4 and similar processes are repeated. On the other hand, when the difference value between the pre-photometric value and the immediate preceding pre-photometric value is greater than the predetermined threshold, the result is NO, a difference value between the pre-photometric value and the target value of light adjustment is calculated and the amount of exposure is calculated and set (step S7).

Next, a post-exposure is executed with a set amount of exposure (step S8), the data of the endoscope image acquired in step S8 is transmitted (step S9), the flow is returned to step S4 and similar processes are repeated.

As described above, when it is determined that the capsule endoscope 10 has moved, images are consecutively picked up at a predetermined interval and when it is determined that the capsule endoscope 10 has not moved, a state continues in which images are not picked up. As a result, a group of images picked up by the capsule endoscope 10 are picked up at random time intervals without being bound by a concept of, for example, 2 frames per second.

The capsule endoscope 10 according to the present embodiment measures brightness by performing pre-exposure and pre-photometry, compares this brightness information with last measured brightness information, detects movement of the capsule endoscope 10 and then picks up an image. For this reason, the capsule endoscope 10 can reduce power consumption without uselessly picking up images.

Furthermore, the capsule endoscope 10 executes a pre-exposure in the pre-exposure area 13a which is part of the region of the image pickup device 13, can thereby shorten the exposure time period and shorten the pre-photometric time period by reducing the exposure area. Moreover, since a pre-exposure and a pre-photometry can be executed in a shorter time period than a post-exposure, it is possible to detect movement of the capsule endoscope 10 faster and pick up images at optimum timing.

Thus, according to the capsule endoscope and the capsule endoscope system of the present embodiment, it is possible to prevent useless image pickup and reduce power consumption.

Second Embodiment

Next, a second embodiment will be described. With the capsule endoscope 10 according to the first embodiment, for example, when an image pickup target region has a large width from dark to bright regions, that is, when the amount of brightness is very small or very large, the photometric value becomes very small or very large, and accurate brightness information may not be acquired. Thus, the capsule endoscope 10 will be described in the second embodiment which can accurately acquire brightness information even when an image pickup target region has a large width from dark to bright regions.

Note that an overall configuration of the capsule endoscope 10 of the second embodiment is similar to that of the first embodiment, and so only components different from those of the first embodiment will be described. In the second embodiment, a plurality of pixel areas are provided in a pre-exposure area. In the following description, the pre-exposure area 13a in FIG. 3 will be described but the pre-exposure areas 13b and 13c may also have similar configurations.

Figure 7:
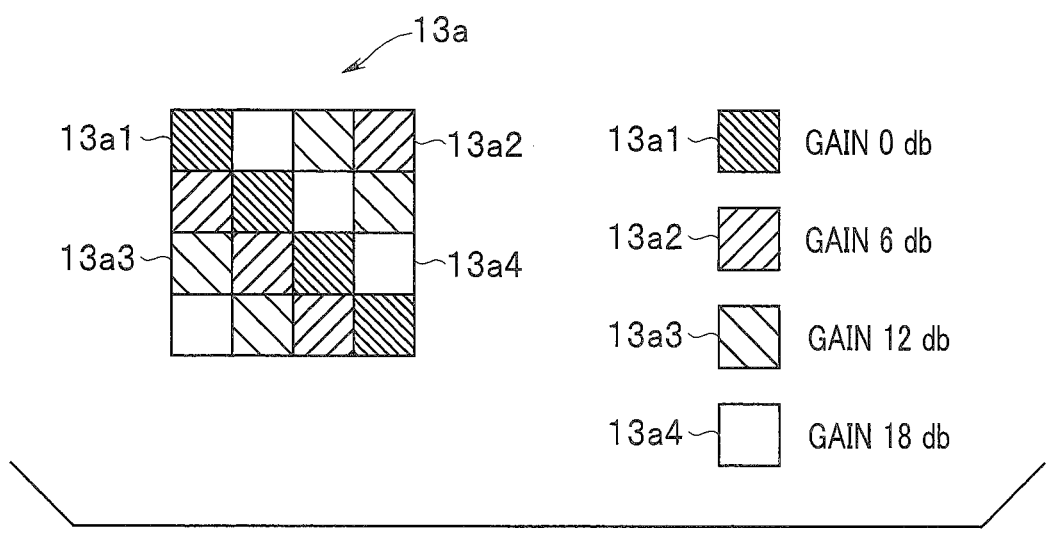

FIG. 7 is an enlarged view of the pre-exposure area 13a. As shown in FIG. 7, the pre-exposure area 13a is constructed of four pixel areas 13a1, 13a2, 13a3 and 13a4, and the pixel areas 13a1, 13a2, 13a3 and 13a4 are arranged in a mosaic pattern. Note that although the pre-exposure area 13a is constructed of the four pixel areas 13a1, 13a2, 13a3 and 13a4, the pre-exposure area 13a is not limited to this, but the pre-exposure area 13a needs only to include at least two or more pixel areas. The pixel areas 13a1, 13a2, 13a3 and 13a4 are not limited to the mosaic arrangement, but may also be arranged in parallel, for example.

Different gains are set for the pixel areas 13a1, 13a2, 13a3 and 13a4 respectively. The pixel area 13a1 is an area with a gain of 0 db whose gain is never increased, the pixel area 13a2 is an area whose gain is increased by 6 db. The pixel area 13a3 is an area whose gain is increased by 12 db and the pixel area 13a4 is an area whose gain is increased by 18 db. Note that the amount of gain increase is not limited to the aforementioned 6 db, 12 db and 18 db, but may be other amounts of gain increase.

The control section 16 compares photometric values acquired in the respective pixel areas 13a1 to 13a4 with photometric values acquired in the respective pixel areas 13a1 to 13a4 through last pre-exposures, determines whether or not the comparison results in all the pixel areas 13a1 to 13a4 fall within a predetermined threshold and detects movement of the capsule endoscope 10.

When the comparison results in all the pixel areas 13a1 to 13a4 fall within the predetermined threshold, the control section 16 determines that the capsule endoscope 10 has not moved, and when the comparison result in at least one of the pixel areas 13a1 to 13a4 is greater than the predetermined threshold, the control section 16 determines that the capsule endoscope 10 has moved.

Next, operation of the capsule endoscope 10 configured in this way will be described.

Figure 8:
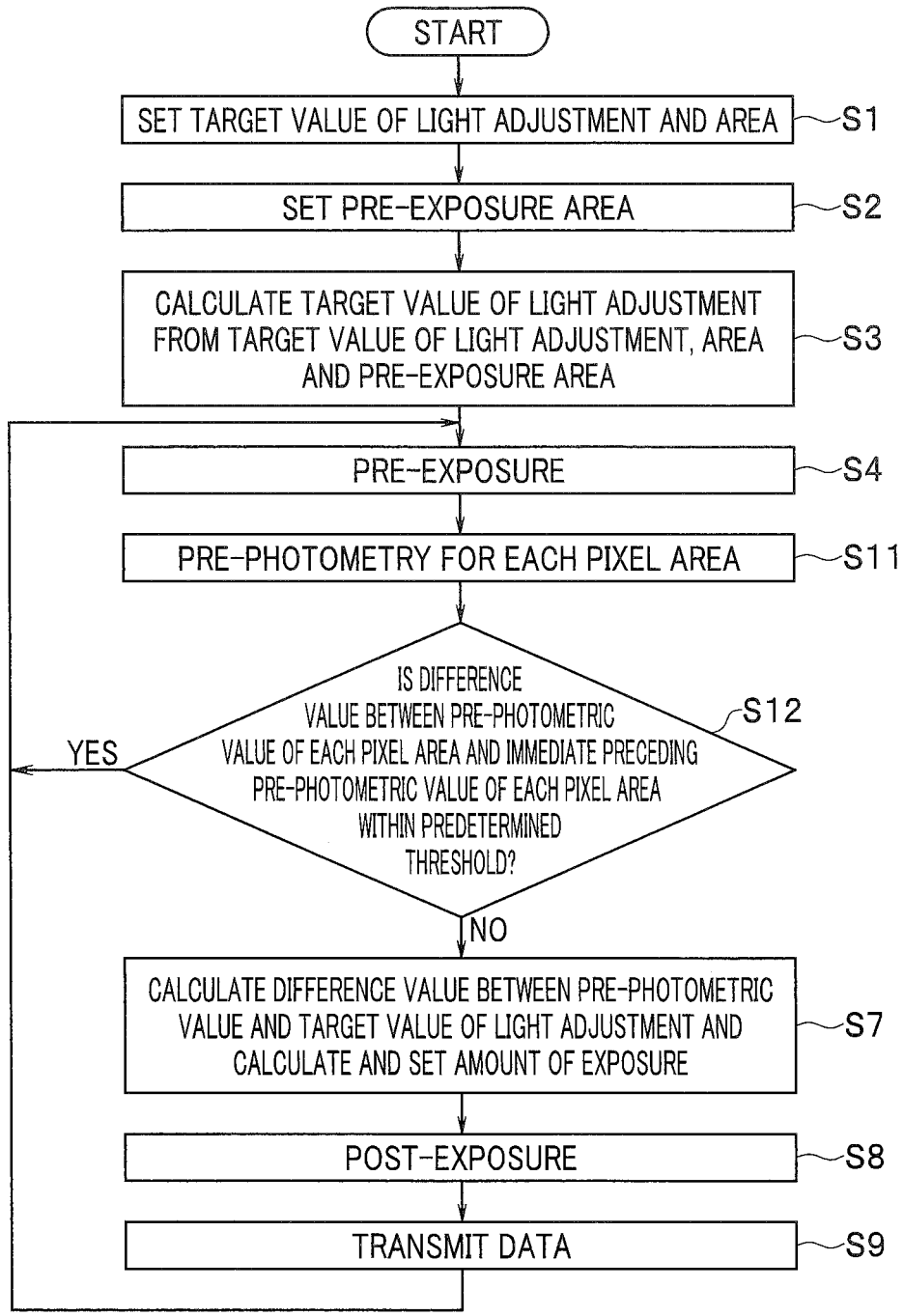
FIG. 8 is a flowchart for describing operation of a capsule endoscope 10 according to a second embodiment.

FIG. 8 is a flowchart for describing operation of the capsule endoscope 10 according to the second embodiment. Note that in FIG. 8, processes identical to those in FIG. 6 are assigned identical reference numerals and description thereof will be omitted.

In step S4, when a pre-exposure is executed, pre-photometry is executed for each pixel area 13a1 to 13a4 (step S11). It is determined whether or not a difference value between a pre-photometric value of each pixel area 13a1 to 13a4 and an immediate preceding pre-photometric value of each pixel area 13a1 to 13a4 falls within a predetermined threshold (step S12).

When it is determined that the difference value between the pre-photometric value of each pixel area 13a1 to 13a4 and the immediate preceding pre-photometric value of each pixel area 13a1 to 13a4 falls within the predetermined threshold, the result is YES, the flow returns to step S4 and similar processes are repeated. On the other hand, when any one difference value between the pre-photometric value of each pixel area 13a1 to 13a4 and the immediate preceding pre-photometric value of each pixel area 13a1 to 13a4 is greater than the predetermined threshold, the result is NO, and the flow proceeds to step S7, the difference value between the pre-photometric value and the target value of light adjustment is calculated and the amount of exposure is calculated and set. Then, in step S8, a post-exposure is executed with the set amount of exposure, the data of the endoscope image acquired in step S8 is transmitted, the flow then returns to step S4 and similar processes are repeated.

As described above, the capsule endoscope 10 according to the present embodiment provides the pixel areas 13a1 to 13a4 having different gains in the pre-exposure area 13a. When, for example, an image pickup target region is dark, the pixel area 13a1 with a gain of 0 db has a very small amount of brightness, and so the photometric value becomes very small and accurate brightness information cannot be acquired, whereas providing the pixel areas 13a2, 13a3 and 13a4 whose gains are increased by 6 db, 12 db and 18 db respectively in a mosaic pattern makes it possible to obtain sufficient photometric information (brightness information) at pixels whose gains are increased to 12 db, for example.

With such a configuration, when, for example, the image pickup target region is bright, the brightness information becomes very large in the pixel areas 13a2, 13a3 and 13a4 whose gains are increased to 6 db, 12 db and 18 db, the photometric values thereby become very large, making it impossible to acquire accurate brightness information, but providing the pixel area 13a1 with a gain of 0 db allows sufficient photometric information to be obtained in pixels where gains are not increased.

As a result, the capsule endoscope 10 of the present embodiment has an effect of being able to widen a dynamic range compared to the first embodiment without changing or increasing the pre-exposure time period.

Note that regarding steps in the respective flowcharts in the Specification, as long as it does not go against the nature of the steps, the order in which steps are executed may be changed, steps may be executed simultaneously or steps may be executed in a different order at each execution.

The present invention is not limited to the aforementioned embodiments, but various modifications or alterations or the like may be made without departing from the spirit and scope of the present invention.

What is claimed is:

1. A capsule endoscope comprising:
   an image sensor configured to perform first exposure for acquiring brightness information and second exposure for picking up an image;
   a memory configured to store the brightness information acquired in the first exposure performed by the image sensor; and
   a controller configured to:
      perform control so as to compare the brightness information acquired in the first exposure performed by the image sensor with brightness information acquired in first exposure performed by the image sensor immediately before acquiring the brightness information and stored in the memory;
      when a comparison result is equal to or less than a threshold, compare brightness information acquired by causing the image sensor to perform first exposure again with the brightness information acquired in the first exposure performed by the image sensor immediately before and stored in the memory; and
      when the comparison result is greater than the threshold, cause the memory to store the image picked up by causing the image sensor to perform the second exposure or cause a transmitter provided in the capsule endoscope to transmit the image to outside the capsule endoscope.

2. The capsule endoscope according to claim 1, wherein the controller is configured to compare the brightness information acquired in the first exposure performed by the image sensor following after storage of the image in the memory or after transmission of the image by the transmitter with the brightness information acquired in the first exposure performed by the image sensor immediately before and stored in the memory.

3. The capsule endoscope according to claim 1, wherein the controller is configured to:
   compare the brightness information acquired in the first exposure performed by the image sensor with the brightness information acquired in the first exposure performed by the image sensor immediately before acquiring the brightness information and stored in the memory at a predetermined interval; and
   perform control, when the comparison result is equal to or less than the threshold, so as to prevent the image sensor from performing the second exposure and prevent the transmitter from performing transmission.

4. The capsule endoscope according to claim 1, wherein the brightness information is acquired from part of pixels of the image sensor including a central pixel of the image sensor.

5. The capsule endoscope according to claim 1, wherein the brightness information is acquired from part of pixels of the image sensor which are pixels of four parts in adjacent areas of four corners of a plane on which image pickup pixels of the image sensor are disposed.

6. The capsule endoscope according to claim 1, wherein the brightness information is acquired from pixels located in adjacent areas of pixels used for display out of pixels of the image sensor and corresponding to positions which are not reproduced or displayed on a screen.

7. The capsule endoscope according to claim 1, wherein the image sensor comprises a first pixel group and a second pixel group, and
   wherein first information for which no gain increase is performed is generated for information obtained from the first pixel group, second information for which a gain increase is performed by a first amount is generated for information obtained from the second pixel group, and the brightness information is acquired based on the first information and the second information.

8. The capsule endoscope according to claim 7, wherein the image sensor further comprises a third pixel group,
   wherein third information for which a gain increase is performed by a second amount greater than the first amount is generated for information obtained from the third pixel group and the brightness information is acquired based on the first information, the second information and the third information.

9. A capsule endoscope system comprising:
   a capsule endoscope comprising:
      an image sensor configured to perform first exposure for acquiring brightness information and second exposure for picking up an image;
      a memory configured to store the brightness information acquired in the first exposure performed by the image sensor; and
      a controller configured to:
         perform control so as to compare the brightness information acquired in the first exposure performed by the image sensor with brightness information acquired in first exposure performed by the image sensor immediately before acquiring the brightness information and stored in the memory;
         when a comparison result is equal to or less than a threshold, compare brightness information acquired by causing the image sensor to perform first exposure again with the brightness information acquired in the first exposure performed by the image sensor immediately before and stored in the memory; and
         when the comparison result is greater than the threshold, cause the memory to store the image picked up by causing the image sensor to perform the second exposure or cause a transmitter provided in the capsule endoscope to transmit the image to outside the capsule endoscope; and
   an external apparatus comprising:
      a receiver configured to receive the image transmitted to outside by the transmitter; and
      an external memory configured to store the image received by the receiver.

* * * * *